United States Patent [19]

Compassi

[11] Patent Number: 5,439,687
[45] Date of Patent: Aug. 8, 1995

[54] DOSAGE FORMS HAVING ZERO-ORDER DIHYDROPYRIDINE CALCIUM ANTAGONIST RELEASE

[75] Inventor: Sabine Compassi, Stansstad, Switzerland

[73] Assignee: Siegfried Pharma AG, Zofingen, Switzerland

[21] Appl. No.: 14,836

[22] Filed: Feb. 8, 1993

[30] Foreign Application Priority Data

Feb. 17, 1992 [CH] Switzerland ............ 00464/92

[51] Int. Cl.⁶ .............. A61K 9/22; A61K 9/36; A61K 9/52
[52] U.S. Cl. .................... 424/468; 424/465; 424/480; 424/482; 424/456; 424/457; 424/488
[58] Field of Search ........... 424/484, 468, 488, 482, 424/480, 464–465, 456–457

[56] References Cited

U.S. PATENT DOCUMENTS

| | | | |
|---|---|---|---|
| 4,412,986 | 11/1983 | Kawata et al. | 514/772 |
| 4,571,333 | 2/1986 | Hsiao et al. | 424/22 |
| 4,654,206 | 3/1987 | Okuda et al. | 424/480 |
| 4,695,467 | 9/1987 | Uemura et al. | 424/502 |
| 4,803,079 | 2/1989 | Hsiao et al. | 424/468 |
| 4,871,548 | 10/1989 | Edgren et al. | 424/464 |
| 4,880,623 | 11/1989 | Piergiornio et al. | 424/465 |
| 4,893,393 | 6/1983 | Schor et al. | 424/19 |
| 4,942,040 | 7/1990 | Ragnarsson et al. | 424/488 |
| 4,966,772 | 10/1990 | Ohm et al. | 424/482 |
| 5,055,306 | 10/1991 | Barry et al. | 424/466 |
| 5,079,237 | 1/1992 | Husu et al. | 514/58 |

FOREIGN PATENT DOCUMENTS 0274176  7/1988  European Pat. Off.
8902738  4/1989  WIPO.

Primary Examiner—Edward J. Webman
Attorney, Agent, or Firm—Mathews, Woodbridge & Collins

[57] ABSTRACT

Pharmaceutical dosage forms having a linear release rate of the $0^{th}$ order for the once-daily oral administration of 20–120 mg of nifedipine or of another calcium antagonist of the dihydropyridine type, characterised by a homogeneous matrix containing 2–50% by weight of hydroxypropylmethylcellulose having an average molecular weight of 20,000–250,000, 5–60% by weight of a calcium antagonist of the dihydropyridine type, as well as customary excipients compatible with the formulation, such as lipophilic or hydrophilic liberation controllers, fillers, flow-regulating agents, lubricants and, optionally, film coatings.

19 Claims, 2 Drawing Sheets

DOSAGE FORMS HAVING ZERO-ORDER DIHYDROPYRIDINE CALCIUM ANTAGONIST RELEASE

FIELD OF THE INVENTION

The invention relates to solid, orally administrable pharmaceutical dosage forms having prolonged active ingredient release for once-daily administration, containing calcium antagonists of the dihydropyridine type as active ingredients.

BACKGROUND OF THE INVENTION

Calcium antagonists of the dihydropyridine type and their uses, for example as cardiovascular agents, are known (see British Patent 1 173 862; British Patent 1 358 951; U.S. Pat. No. 4,256,749; DE-OS 33 11 003). Those compounds, such as nifedipine, which is one of the most well known representatives of the group, are used especially for the treatment of coronary heart disease, for the prophylaxis of attacks of Angina pectoris and for the treatment of hypertension.

Various dosage forms are known which, depending upon the galenical characteristics, are suitable in various forms for the treatment of the above indications. Attention should be paid especially also to the physicochemical properties of the substance. Nifedipine and other calcium antagonists of the dihydropyridine type are only very slightly soluble in water. For example, a maximum of 10 mg of nifedipine is soluble in 1000 ml of simulated gastric or intestinal fluid (0.001%). Solubilities of less than 0.3% in aqueous media are likely to give rise to absorption problems which manifest themselves in a reduction in the rate of absorption and in the amount absorbed (Barker et al.; Austral. J. Pharm. 49, 33–43, 1968).

For example, crystalline nifedipine is absorbed so slowly that the pharmacokinetic elimination rate exceeds the absorption rate. In comparison with capsules containing nifedipine in dissolved form, this results in plasma levels that are relatively low but fall more slowly (so-called Flip-Flop; Wagner JG., Fundamentals of Clinical Pharmacokinetics, Hamilton, III. 1975, Drug Intelligence Publications). For example, according to G. Pabst et al., Arzneim.-Forsch./Drug Res. 36(1), 256–260, 1986, after the administration of 20 mg of dissolved nifedipine in capsules, plasma level peaks of about 200 ng/ml are found as early as after about 30 minutes. After the administration of the same dose of crystalline nifedipine, the plasma level peaks after about 1.5 hours are about 40 ng/ml. Nifedipine dissolved in capsules therefore achieves plasma levels that are high but fall rapidly, whereas the administration of the same dose in crystalline form in tablets results in plasma levels that are lower but longer lasting.

Nifedipine in capsules is used especially when an immediate effect is required (treatment of an attack of Angina pectoris, treatment of hypertensive crises). The dosage is then 3×5 mg, 3×10 mg or 3×20 mg daily. However, the rapid rate of nifedipine influx increases the risk regarding reflex tachycardia.

In order to attain and maintain constant levels of active ingredients in the plasma there are used, on the one hand, infusion solutions, which are, however, unsuitable for ambulant treatment, or, on the other hand, retard preparations from which the active ingredient is released only in a delayed manner into the biological system.

Nifedipine in crystalline form is therefore especially suitable, for example, for long-term ambulant treatment of hypertension or coronary heart disease. The most customary dosage is 2×20 mg daily. In many cases the dosage has to be increased to 2–3×40 mg per day. The solubility behaviour and thus also the absorption rate can be controlled to a certain degree via the crystal size of nifedipine (EP 47 899).

For the manufacture of retard preparations it is also possible to use amorphous nifedipine by controlling the superior solubility of the non-crystalline form in comparison to the crystalline form, by using suitable excipients (EP 232 155; EP 220 760; DE-OS 30 24 858). Several possible methods of manufacturing amorphous nifedipine preparations having improved solubility behaviour on the basis of the molecularly disperse presence of the substance have been disclosed (cf. DE-OS 28 22 882). The preparation of amorphous nifedipine generally requires organic solvents, there being used especially methylene chloride because of its excellent dissolving power. Where possible, however, chlorinated hydrocarbons should be avoided in the manufacture of modern medicaments. Ethanol is a less efficient solvent, since nifedipine is much less soluble therein and therefore large amounts of solvent are required. In addition, in the amorphous state the material is generally unstable and may change into the more stable crystalline form again, for which triggering factors include heat and moisture.

Known pharmaceutical preparations having delayed release of nifedipine, for example AdalatR retard or CorotrendR retard, involve especially twice daily administration and, as in vitro tests show, release 60–90% of the total dose of the medicinal substance within 8 hours (see Table 1). The lowest plasma levels regarded as still being effective, approximately 10–15 ng/ml, are attained as early as 6 to 8 hours after the administration of 20 mg (see Pabst and EP 220 760). When a tablet containing 40 mg of nifedipine is used, the plasma levels after 12 hours fluctuate above the necessary minimum effective concentration (EP 220 760), but the 40 mg form described rapidly attains plasma level peaks of more than 60 ng/ml initially which then, in accordance with the specific elimination kinetics (Flip-Flop model), fall to about 20–25 ng/ml within the first 9 hours. After 16 hours the concentrations are about 15–17 ng/ml and after 24 hours they are still about 8–11.4 ng/ml. That plasma level behaviour is not optimum for once-daily administration, since in order to obtain plasma levels above the minimum effective threshold during the second twelve hours it is necessary to accept high plasma levels during the first 12 hours. As mentioned above, the rapid influx rate of nifedipine in conjunction with high plasma level peaks has repeatedly been associated with an increased side-effect rate (tachycardia) and reduced effectiveness in lowering blood pressure (Kleinbloessem et al.; Clin. Pharmacol. Ther. 35,6, 742–749, 1984).

Accordingly, it would be desirable to have nifedipine formulations that are distinguished by a slow influx rate and small plasma level fluctuations, that is to say plasma levels that remain constant over a relatively long period. That medicament should provide, as early as on the first administration or on repeated administration, constant, therapeutically effective plasma levels exhibiting a minimum of fluctuations between the maximum and minimum concentrations of active ingredient in the blood. A possible method of reducing the influx time of the active ingredient and of minimising fluctuations lies in controlling the dissolution of the active ingredient over an even longer period of time than is the case with conventional retard formulations. That requires the active ingredient to be absorbed over the entire gastro-intestinal tract.

A solution to this problem is offered by the therapeutic system OROS$^R$ (F. Theeuwes, J. Pharm. Sci., Vol. 64,12, 1987-1991, 1975) which has already been described for sparingly soluble active ingredients with a double chamber system (U.S. Pat. No. 4,111,202) and especially for nifedipine (BE 898 819). It can be seen from Table 1 that the system containing 30 mg of nifedipine releases only about 20% of the total dose after the first 8 hours. The liberation rate from the third hour is linear, that is to say about 3.33-4% (i.e. 0.9-1.2 mg) of the total dose are released per hour. That release principle differs quite clearly from the dissolution curves of conventional retard forms for twice-daily administration in which after 8 hours 60-100% of the dose, generally 20 mg, are released with a non-linear profile (Table 1). Using the OROS therapeutic system it is possible with 30 mg of nifedipine to maintain plasma levels of approximately 10-20 ng/ml over a period of 24 hours without the necessity to accept plasma level peaks. A disadvantage of the OROS systems is that they are technically difficult to produce.

The release rate from tablets or powders is influenced by the solubility characteristics of the active ingredient which, in turn, depend upon particle size, specific surface area and interactions with excipients. Dissolution can be retarded by means of diffusion barriers in the core of the tablet or in a film coating. Retarding dissolution by means of diffusion barriers in the core is a principle that is frequently used on account of its technical simplicity. It is possible to use various excipients, for example swelling agents, lipophilic substances or alternatively plastics, as diffusion barriers. The matrix, that is to say the homogeneous substance composition, can be such that the release of the active ingredient takes place by diffusion of the dissolved active ingredient especially through the water-filled pores in the tablet core and if required in special cases by diffusion through the retarding substance which must for that purpose be in a suitable structural form. Alternatively the matrix also can be in a form that is subjected to slow erosion and in this way effects delayed release of the active ingredient.

In all those cases the diffusion path and the active diffusion surface for the release change with time. For that reason it is clear that with matrix systems neither in vivo nor in vitro is it usually possible to expect any release having linear kinetics, that is to say of the $0^{th}$ order. Instead, the release is generally a function of the root of the time (Square root dissolution; Higuchi; J. Pharm. Sci. 52,12,1963, 1145). The validity of the Higuchi law for the hydrocolloid matrix has also been documented in numerous publications (Ford et al., Int. J. Pharm., 24, 1985, 327-338; 339-350; 1985).

Therapeutic dosage forms in which the medicinal substance is incorporated into a soluble or erodible matrix would be desirable per se on account of the ease of their manufacture, the low degree of variation between different manufacturing processes and because of the relatively low costs.

The use of hydrophilic gums, such as hydroxypropylmethylcellulose, as delaying matrix material is known and has been tested with a large number of active ingredients, but no formulation has been disclosed hitherto that would be suitable for attaining the desired objectives with calcium antagonists of the dihydropyridine type, such as nifedipine.

The behaviour of a specific medicinal substance when combined with a retarding excipient cannot be calculated or generally predicted. Although the basic factors affecting release from matrix systems have been well researched, interactions between the retarding material on the one hand and the active ingredient and other excipients on the other can affect the retarding action in various ways.

In particular, the manufacture of monolithic matrix forms having a release profile according to the $0^{th}$ order is one of the important problems of galenical pharmacy. Long-term release systems that obey the Higuchi law of release are disadvantageous because the release rates decline markedly with time.

A release rate of the $0^{th}$ order is difficult to produce because, as mentioned, for geometric reasons lengths of diffusion path for the active ingredient that are dependent upon time and rate of release have to be overcome. The release rate decreases as the length of the diffusion path increases, that is to say as time passes less and less substance is released.

It is therefore remarkable that in certain cases and under favourable conditions both readily soluble and sparingly soluble medicinal substances exhibit a linear dissolution principle from matrix systems containing hydroxypropylmethylcellulose (HPMC) (Ranga Rao et al., Drug Development and Industrial Pharmacy, 14 (15-17), 2299-2320, 1988 and Ranga Rao et al., J. of Controlled Release, 12, 1990, 133-141). The solubility of the medicinal substance is therefore not absolutely critical for release of the $0^{th}$ order.

The question of release kinetics is a multi-factored problem in which, in addition to the dissolution properties of the active ingredient, a part is played by the rate of water absorption and thus the rate of swelling of the interface to be penetrated, the diffusion coefficient of the substance through the swollen mass and also the time-dependent thickness thereof. It can clearly be imagined that release of the $0^{th}$ order is brought about by the existence of an equilibrium between the erosion of the tablet and the dissolution of the active ingredient, so that the diffusion paths for the substance remain constant over the dissolution time. Such a pharmaceutical dosage form cannot be prepared without inventive activity.

Published data of S. Leucuta et al. (Pharmazie, 43, 1988, 845 ff) show, in addition, that the Higuchi release kinetics are observed in the case of a nifedipine/HPMC system under customary conditions.

PROBLEM OF THE INVENTION

The problem underlying the present invention is to overcome the existing prejudices by developing a solid, orally administrable pharmaceutical dosage form for sparingly water-soluble calcium antagonists that are absorbable over the entire gastro-intestinal tract, especially for nifedipine, that is technically easy to produce and is suitable for maintaining a constant, therapeutically effective level of active ingredient in the plasma over a period of approximately 24 hours with a once-daily oral administration. This represents the development of a medicament in which release is delayed to a greater extent than in conventional retard forms (Adalat retard 20), there being sought in vivo a release profile that is as linear as possible, that is to say a therapeutic medicament to be characterised over a period of several hours essentially by a dissolution process of the $0^{th}$ order. Since the active ingredient, once dissolved in the gastro-intestinal tract, is absorbed rapidly and since only the kinetics of the release will be the rate-limiting factor for absorption, a constant rate of release in vivo could maintain the absorption rate at a constant value. As a result of this dissolution process of the $0^{th}$ order, it is possible to achieve infusion-like pharmacokinetic conditions. Conversely, infusion-like pharmacokinetic conditions after the administration of a medicament indicate an absorption rate of the 0th order or, in the case of release-limited absorption, an in vivo release of the $0^{th}$ order.

As mentioned above, a constant rate of release of the $0^{th}$ order from solid dosage forms, such as tablets or powder capsules, is not what would immediately be expected of sparingly soluble active ingredients and is difficult to achieve since many parameters must be taken into account.

It can be seen from the above comments that release kinetics of the $0^{th}$ order are not to be expected a priori with sparingly soluble calcium antagonists of the dihydropyridine type, such as nifedipine, with HPMC systems. Release kinetics of the $0^{th}$ order are to be regarded as a special case which may occur only with certain dosage forms. From the large number of known pharmaceutical excipients it is necessary to select those suitable for the desired purpose and to process them in suitable quantity ratios, which must likewise be selected, to form a matrix system. Such dosage forms are provided by the formulations according to the invention.

DETAILED DESCRIPTION OF THE INVENTION

The invention relates to a pharmaceutical dosage form having prolonged release of the active ingredient, suitable for maintaining a therapeutically effective plasma level over a period of 24 hours with a once-daily oral administration, containing as active ingredient a therapeutically effective amount of a sparingly water-soluble calcium antagonist of the dihydropyridine type, characterised by a homogeneous matrix containing 5-60% by weight of a crystalline, sparingly water-soluble calcium antagonist of the dihydropyridine type, 2 to 50% by weight of hydroxypropylmethylcellulose having a molecular weight in the range of about 20,000-250,000, optionally 2-25% by weight of pharmaceutically acceptable excipients controlling release and optionally other pharmaceutically acceptable excipients making up the weight of the dosage form to 100%.

SHORT DESCRIPTION OF THE FIGURES

Figure 3:
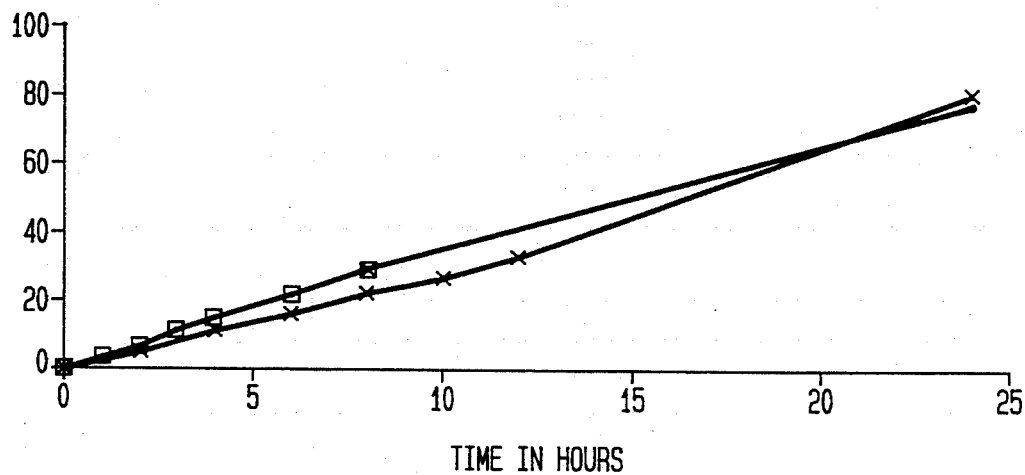

FIG. 3 shows the correlation of the in vivo absorption rate up to 24 hours, calculated according to Wagner-Nelson, J. Pharm. Sci. 52, Vol. 6, 1963, page 610–611,(—·—) and the in vitro dissolution rate in simulated intestinal fluid of the nifedipine tablet according to Example 8 during 8 (—□—)and 24 hours (—x—).

The curves are of $0^{th}$ order and indicate the good in vitro/in vivo correlation. In vitro dissolution results are obtained by the method of Langenbucher et al., Pharm. Ind. 51, 11, 1989, page 1276–1281. The media used are simulated intestinal fluid (sif) of pH $7.2\pm0.2$, containing 8.05 g of disodium hydrogenphosphate, 1.56 g of disodium dihydrogenphosphate and demineralised water up to 1000 ml, and simulated gastric fluid containing 2.0 g of sodium chloride, 80.0 ml of 1N hydrochloric acid and demineralised water up to 1000.0 ml.

Pharmaceutical dosage forms are especially tablets and powders introduced into capsules, for example hard gelatin capsules.

Prolonged release of the active ingredient is to be understood as being especially a rate of release over a period of approximately 24 hours that increases slowly at first and is then substantially constant per unit of time over a period of several hours (release of the $0^{th}$ order).

A therapeutically effective plasma level is to be understood as being more than 10 ng of active ingredient, for example nifedipine, per ml of plasma.

A therapeutically effective amount is the amount required for maintaining the desired therapeutic effect over a period of approximately 24 hours, that is to say from 20 to 120 mg of active ingredient, preferably 20, 30, 40, 50, 60, 70, 80, 90, 100 or 120 mg.

Sparingly water-soluble calcium antagonists of the dihydropyridine type are those which have approximately the same water-solubility as nifedipine, that is to say that are about 0.001% soluble, or alternatively are slightly less or more soluble, for example approximately from 0.0001 to 0.01% soluble, in aqueous, simulated gastric or intestinal fluid. Special mention should be made of nifedipine and also of nitrendipine. Other calcium antagonists of this type are, for example, nimodipine, isradipine, nicardipine, niludipine, nigludipine, nisoldipine, felodipine, amlodipine and lacidipine. According to the invention, those active ingredients are in crystalline form. The specific surface area thereof is, for example, approximately $0.2-0.5 \text{ m}^2/\text{g}$ (BET), preferably $0.3-0.4 \text{ m}^2/\text{g}$.

A matrix is defined in galenical pharmacy as being a well mixed, homogeneous substance composition that can be compressed to form tablets or can be introduced in the form of a powder into capsules, in this instance preferably hard gelatin capsules.

The tablets or capsules contain, for example, 20–120 mg, preferably 20, 30, 40, 50, 60, 70, 80, 90, 100 or 120 mg, of active ingredient, for example nifedipine or alternatively nitrendipine.

The hydroxypropylmethylcellulose (HPMC) used according to the invention represents the retarding principle, is preferably of the 2208 USP XXII type, has a molecular weight of 20,000–250,000, preferably 20,000–120,000, and has a preferred viscosity of 100–100,000, preferably 100–15,000 cps. Especially suitable are Methocel K types which produce the fastest swelling, for example Methocel K100LV, Methocel K4M and Methocel K15M (brand names, DOW CHEMICAL CO.) or the virtually equivalent Metolose 90SH types, for example Metolose 90SH100, Metolose 90SH4,000 and Metolose 90SH15,000 (brand names, Shin-Etsu Chemical Co. Ltd.). Approximately 2–50% by weight HPMC are used, based on the final weight of the tablet or capsule filling.

The pharmaceutically acceptable excipients controlling release are lipophilic or hydrophilic substances (release retarders, liberation controllers) that modify the swelling process of the retarding matrix. Hydrophilic release retarders are solid polyethylene glycols, for example polyethylene glycol 4,000 or 6,000, or polyvinylpyrrolidones, for example Kollidone 25, Kollidone 30 or Kollidone 90 (brand names of BASF GmbH) having various viscosities, and also vinylpyrrolidone/vinyl acetate copolymers, for example Kollidone VA 64 (brand name BASF GmbH). Lipophilic release retarders are pharmaceutically acceptable derivatives of vegetable fats in solid, tablet-table form having a melting point of above 60°, such as vegetable fatty acids having chain lengths of at least 16 carbon atoms, for example stearic acid C16, palmitic acid C18 or mixtures thereof, and especially vegetable oils hardened by hydrogenation, for example hydrogenated castor oil, such as Cutina HR (brand name of Henkel) or hydrogenated cottonseed oil, such as Emvelop or Lubritab (brand names of Mendell). For the preparation of tablets the lipophilic release retarders must be suitable for tabletting. Optionally 2-25% release retarder are used, based on the final weight of the tablet or capsule and in dependence of the nature of the retardation of release desired.

Further excipients are certain fillers, lubricants and flow-regulating agents, which may likewise exert an effect, albeit a small one, on the release kinetics.

Fillers are corn starch, lactose, powdered and microcrystalline cellulose, mannitol or dicalcium phosphate, and also mixtures thereof. Preferred is a mixture of 75% lactose and 25% powdered cellulose, for example Cellactose (brand name of Meggle GmbH). The fillers must therefore be carefully selected in suitable amounts and matched exactly to the specific formulation. In addition, attention should be paid to the compression properties. They are used in an amount making up the weight of the tablet to 100%.

Lubricants are, for example, magnesium stearate, stearic acid of a suitable quality, calcium stearate, and mixtures thereof, magnesium stearate being preferred, and are preferably used in an amount of 0.2-1%, based on the final weight of the formulation. Suitable agents that act on the flowability of the powder to be encapsulated or compressed (flow-regulating agents) are, for example, highly dispersed silicon dioxide, preferably in an amount of 0 25-1% based on the final weight of the formulation.

The tablets can be provided with a neutral film coating or with a film coating that delays the release of the active ingredient, that is to say that produces a lag time.

A film coating having no retarding action on the active ingredient consists, for example, of film-formers, pigments, anti-adhesive agents and plasticisers. Such a film former may consist of fast-dissolving constituents in which case it is preferable to use low-viscosity hydroxypropylmethylcellulose type 2910 USP XXII, for example Methocel E5 or E 15 (Dow Chemicals Ltd.) or Pharmacoat 606 (Shin-Etsu).

A film coating having retarding action on the active ingredient may consist of water-insoluble but water-permeable polymers which, as a diffusion barrier, not only bring about a lag time at the beginning but also affect the swelling behaviour of the core over a prolonged period as a result of the initially altered water permeation. Preferred water-insoluble polymers are water-insoluble derivatives of methacrylic acid, for example methyl/ethyl acrylate, such as Eudragit RS or RL and Eudragit NE (brand names, Röhm Pharma GmbH) and mixtures thereof. The dosage of said film coating polymers should be adapted to the retarding effect desired and is, for example, 1-1.5 mg/cm$^2$ surface area.

The film coating may also contain excipients customary in film-coating procedures, such as light-protective pigments, for example iron oxide, in an amount of approximately 40-80%, or titanium dioxide, in an amount of 100-150 %, anti-adhesive agents, for example talc, in an amount of approximately 50-200%, and also suitable plasticisers, matched to the polymer, of the polyethylene glycol series, for example PEG 400 or PEG 6,000, or triethyl citrate in the case of films based on methacrylic acid derivatives, such as Eudragit RS/RL and NE, in an amount of approximately 30-60% (percentages are in each case based on the dry coating substance). When aqueous dispersions of the said Eudragit types are used, then, for example, Tween 80 is necessary as aggregation inhibitor.

For the preparation of the powder components for filling hard gelatin capsules it is possible to use the same powder components as those used for the preparation of tablets; surprisingly the same release profiles are achieved.

The release kinetics in tablets are also dependent upon geometric factors, such as the shape and size of the tablets. Biconvex tablets having a diameter of approximately 5-11 mm, especially 7-9 mm, and a thickness of 3-5 mm, especially 4 mm, are preferred.

Preferred tablets contain, for example:

40 mg of nifedipine or alternatively nitrendipine,
approximately 2-35 mg of hydroxypropylmethylcellulose type 2208 USP XXII of 100 or 4000 cps,
approximately 20-50 mg of lactose and 35 to 60 mg of powdered and/or microcristalline cellulose, or instead approximately 50-80 mg of a mixture of 75% lactose and 25% powdered cellulose (CellactoseR, Meggle),
optionally approximately 10 mg of hardened vegetable oil,
approximately 1.5 mg of magnesium stearate,
optionally 0,25-1 mg of highly dispersed silicon dioxide, so that cores prepared therefrom weigh 140-155 mg, and are optionally provided with a coating containing
approximately 1.5-2.5 mg of titanium oxide, and
approximately 0.5-1.5 mg of red iron oxide,
approximately 1-3.0 mg of talc,
optionally approximately 2.0 mg of hydroxypropylmethylcellulose type 2910 having a viscosity of 5 to 15 cps,
optionally 1-1.5 mg of polyethylene glycol 400,
optionally approximately 0.005 mg of polysorbate 80,
optionally approximately 0,5-0.75 mg of triethyl citrate,
optionally approximately 0.5-1.5 mg of Eudragit RL dry substance, and/or
optionally approximately 0.5-1.5 mg of Eudragit RS dry substance.

For tablets containing 20, 30, 50, 60, 70, 80, 90, 100 and 120 mg of active ingredient, corresponding aliquots of the excipients should be used.

Preferred pharmaceutical dosage forms are those in which the constant rate of release of active ingredient is about 0.1-4 mg/h, especially about 1-3.5 mg/h, for the dosage form containing 40 mg, and specifically the tablets described in the Examples, in particular Examples 3, 5, 7 and 8.

The release rates of the tablets according to Examples 1 to 7 in simulated gastric fluid, determined by the through-flow method (1 liter/h) and HPLC analysis of the nifedipine released, are shown in Table 1. For comparison purposes, the Table shows the release rates, determined in the same way, for the commercially available, conventional retard formulations Adalat retard 20 mg and Nifhexal retard 40 mg, and also for the formulations of nifedipine that are suitable for once-daily administration, the OROS formulations Procardia XL 30 mg and XL 60 mg.

TABLE 1

| | Rates of release (mg/h) in simulated gastric fluid | | | | | | | | |
|---|---|---|---|---|---|---|---|---|---|
| time h | 0 | 1 | 2 | 3 | 4 | 5 | 6 | 7 | 8 |
| Adalat 20 mg | 0.0 | 4.4 | 2.4 | 1.8 | 1.2 | 1.4 | 1.0 | 1.0 | 0.8 |
| Nifhexal 40 mg | 0.0 | 6.0 | 6.0 | 4.6 | 3.6 | 2.7 | 2.3 | 1.8 | 1.6 |
| Procardia XL 30 mg | 0.0 | 0.0 | 0.0 | 0.0 | 1.0 | 0.7 | 1.0 | 1.4 | 1.3 |
| Procardia XL 60 mg | 0.0 | 0.0 | 0.0 | 0.5 | 1.3 | 2.0 | 2.3 | 2.5 | 2.6 |
| Example 1 40 mg | 0.0 | 1.1 | 2.1 | 2.7 | 3.0 | 3.6 | 3.8 | 3.5 | 3.2 |
| Example 2 40 mg | 0.0 | 0.0 | 0.2 | 0.4 | 0.8 | 0.8 | 1.6 | 1.4 | 1.6 |
| Example 3 40 mg | 0.0 | 0.4 | 0.7 | 0.9 | 1.4 | 1.7 | 2.1 | 2.6 | 2.6 |
| Example 4 40 mg | 0.0 | 0.7 | 1.1 | 1.5 | 1.5 | 1.4 | 1.4 | 1.4 | 1.3 |
| Example 5 40 mg | 0.0 | 0.6 | 1.1 | 1.2 | 1.4 | 1.4 | 1.4 | 1.4 | 1.4 |
| Example 6 40 mg | 0.0 | 1.1 | 1.2 | 1.2 | 1.2 | 1.2 | 1.2 | 1.3 | 1.3 |
| Example 7 40 mg | 0.0 | 1.0 | 0.9 | 1.3 | 1.2 | 1.4 | 1.4 | 1.4 | 1.4 |

Table 1a shows, in mg, the total amounts of active ingredient released after 8 hours in % of the initial dose.

TABLE 1a

| Amount released after 8 hours in simulated gastric fluid | | | |
|---|---|---|---|
| | | % | mg |
| Adalat | 20 mg | 70 | 14.0 |
| Nifhexal | 40 mg | 72 | 28.6 |
| Procardia XL | 30 mg | 18 | 5.5 |
| Procardia XL | 60 mg | 19 | 11.2 |
| Example 1 | 40 mg | 58 | 23.0 |
| Example 2 | 40 mg | 17 | 6.8 |
| Example 3 | 40 mg | 31 | 12.4 |
| Example 4 | 40 mg | 26 | 10.3 |
| Example 5 | 40 mg | 25 | 9.9 |
| Example 6 | 40 mg | 24 | 9.7 |
| Example 7 | 40 mg | 25 | 10.0 |

The mean values, found using the tablets according to Examples 3 and 5, for plasma levels after a single oral administration in comparison with those of Oros system Procardia XL 30 mg and Adalat retard 40 mg (2×20 mg) are shown in Table 2:

TABLE 2

| Mean values (ng/ml) for plasma levels after a single oral administration | | | | |
|---|---|---|---|---|
| time h | Example 5 40 mg | Example 3 40 mg | Procardia XL 30 mg | Adalat retard 40 mg (2 × 20) |
| 0.0 | 0.00 | 0.00 | 0.00 | 0.00 |
| 0.5 | 3.15 | 2.05 | 0.00 | 24.09 |
| 1.0 | 5.49 | 5.61 | 0.00 | 37.74 |
| 2.0 | 11.43 | 10.43 | 0.24 | 49.21 |
| 3.0 | 17.06 | 17.91 | 4.86 | 54.50 |
| 4.0 | 15.38 | 18.16 | 6.61 | 43.20 |
| 6.0 | 13.30 | 17.65 | 11.21 | 32.63 |
| 8.0 | 13.39 | 17.53 | 12.46 | 25.33 |
| 10.0 | 12.35 | 15.88 | 13.54 | 20.98 |
| 12.0 | 12.45 | 14.25 | 16.34 | 17.24 |
| 24.0 | 12.83 | 11.69 | 13.86 | 8.09 |
| 36.0 | 4.41 | 3.4 | 5.33 | 1.81 |
| 48.0 | 2.01 | 2.75 | 1.41 | 0.66 |

The invention relates also to a process for the preparation of a pharmaceutical dosage form according to the above description, characterised in that the dosage form is prepared in a conventional manner.

The constituents of the tablet cores are, if necessary, ground to the desired particle size, mixed homogeneously with one another at the same time or in a specific sequence and, optionally, granulated by moistening with water, dispersing and drying the granular mass. If the mixture is granulated, the fillers, flow agents and lubricants can be added to the granules after granulation. The mixture of the core constituents is compressed to form tablets having a hardness of approximately 50-100N, preferably 80N, or is introduced as such into hard gelatin capsules.

The film-coating is effected in a conventional manner by mixing the constituents of the film coating with water, coating the compressed tablet cores therewith and drying at approximately from 30° to 40° C., preferably approximately 35° C.

The invention relates also to the use of a pharmaceutical dosage form in accordance with the present invention for the treatment of diseases that can be influenced by calcium antagonists, for example hypertension, comprising the once-daily oral administration of a pharmaceutical dosage form according to the present invention containing a therapeutically effective amount of a dihydropyridine derivative to a patient to be treated with calcium antagonists, for example a patient suffering from hypertension.

Depending upon the age and weight of the patient, the nature and severity of the illness as well as the general condition of the patient and also the dihydropyridine derivative to be administered, the dosage forms used contain 20, 30, 40, 50, 60, 70, 80, 90, 100, 110 or 120 mg of active ingredient.

The following Examples illustrate the invention but do not constitute a limitation thereof.

Example 1: Tablets containing 40 mg of nifedipine

For the preparation of 22,000 tablets, 880 g of nifedipine having a specific surface area of 0.3-0.4 m²/g (BET), 440.0 g of HPMC 2208 100 cps (Methocel K100LV), 880.0 g of lactose and 533.5 g of microcrystalline cellulose (Avicel PH 101) are mixed together. The powder mixture is granulated with deionised water. The pre-dispersed and sieved (mesh size 1 mm) granular mass is dried for several hours at 40° C. in vacuo and, if necessary, ground in a hammer mill and sieved again (mesh size 1 mm).

533.5 g of microcrystalline cellulose (Avicel PH 102) are then mixed in. For a ready-to-compress mixture, 33.0 g of magnesium stearate are also mixed in.

The granular mixture is compressed to form biconvex cores having a diameter of 7 mm, a thickness of 4 mm and a hardness of 80N.

The release values in simulated gastric fluid are given in Table 1.

Example 2: Film-coated tablets containing 40 mg of nifedipine

The cores from Example 1 are provided with a film coating using a mixture containing 70.0 g of talc, 50.0 g of titanium oxide, 22.5 g of red iron oxide, 0.125 g of polysorbate 80, 15.0 g of triethyl citrate, 82.5 g of Eudragit RL 30 D, 55.0 g of Eudragit RS 30 D and 990 g of water. The film-coated tablets are dried in a circulating air drying cabinet for at least 4 hours at 35° C.

The release rates in simulated gastric fluid are given in Table 1.

The release profile shows a pronounced lag time. Although the film coating disintegrates after about 1–2 hours, there is a marked reduction in the release rate in comparison with Example 1.

Example 3: Film-coated tablets containing 40 mg of nifedipine

For the preparation of 22,000 tablets, 616.0 g of HPMC 2208 100 cps (Methocel K 100 LV), 220.0 g of hardened, hydrogenated vegetable oil, 22.0 g of silicon dioxide and 33.0 g of magnesium stearate are mixed together.

880.0 g of nifedipine having a specific surface area of 0.3–0.4 $m^2/g$ (BET) and 1529.0 g of a mixture containing 75% lactose and 25% powdered cellulose as a unitary product (Cellactose, Meggle) are added to the above powder mixture and mixed in.

The powder mixture is compressed to form tablets weighing 150 mg and having a diameter of 7 mm, a thickness of 4 mm and a hardness of 80N.

The cores are provided with a film coating using a colloidal dispersion containing 50.00 g of hydroxypropylmethylcellulose (type 2910, viscosity 5 mPas), 27.50 g of polyethylene glycol 400, 50.00 g of titanium dioxide and 22.50 g of red iron oxide, 25.00 g of talc in 1375 g of water.

The film-coated tablets are dried in a circulating air drying cabinet for at least 4 hours at 35° C.

The release values of the cores and of the film-coated tablets in simulated gastric fluid are the same and are given in Table 1.

The mean values for the plasma levels over a period of 48 hours in eight human test subjects after administration of 40 mg are given in Table 2.

Example 4: Hard gelatin capsules containing 40 mg of nifedipine

For the manufacture of 22,000 capsules, 616.0 g of HPMC 2208 100 cps (Methocel K 100 LV) and 880.0 g of nifedipine having a specific surface area of 0.3–0.4 $m^2/g$ are mixed together and granulated with deionised water.

The granular mass is dried in vacuo at temperatures of 40° C. and ground in a hammer mill. 1529.0 g of a mixture containing 75% lactose and 25% powdered cellulose (commercially available unitary product Cellactose, Meggle), 220.0 g of hardened, hydrogenated vegetable oil, 22.0 g of silicon dioxide and 33.0 g of magnesium stearate are mixed into the granules.

The granules are introduced into hard gelatin capsules. The filling weight of the capsules is 150 mg. In order to protect the nifedipine against the action of light, the capsules contain pigments, such as iron oxide/titanium oxide.

The release values in simulated gastric fluid are given in Table 1.

Example 5: Film-coated tablets containing 40 mg of nifedipine

For the preparation of 22,000 tablets, 440.0 g of HPMC 2208/4,000 cps (Methocel K4M or Metholose 90 SH 4,000), 880.0 g of nifedipine having a specific surface area of 0.3–0.4 $m^2/g$ (BET), 880.0 g of a commercially available unitary product consisting of 75% lactose and 25% powdered cellulose (Cellactose, Meggle) and 1067.0 g of microcrystalline cellulose are mixed together. For a ready-to-compress mixture, 33.0 g of magnesium stearate are added and the mixture is compressed to form tablets weighing 150 mg and having a diameter of 7.0 mm, a thickness of 4 mm and a hardness of 80N.

The tablets are provided with the coating described in Example 3.

The release values of the cores and of the film-coated tablets in simulated gastric fluid are the same and are given in Table 1.

The mean values for the plasma levels over a period of 48 hours in eight human test subjects after administration of 40 mg are given in Table 2.

Example 6: Film-coated tablets containing 40 mg of nifedipine

For the preparation of 22,000 tablets, 440.0 g of HPMC 2208/4,000 cps (Methocel K4M or Metholose 90SH-4,000) and 880.0 g of nifedipine having a specific surface area of 0.3–0.4 $m^2/g$ (BET) are granulated in accordance with Example 4.

880.0 g of a commercially available unitary product consisting of 75% lactose and 25% powdered cellulose (Cellactose, Meggle) and 1067.0 g of microcrystalline cellulose are mixed into the granules. For a ready-to-compress mixture, 33.0 g of magnesium stearate are added and the mixture is compressed to form tablets weighing 150 mg and having a diameter of 7.0 mm, a thickness of 4 mm and a hardness of 80N.

The tablets are provided with the coating described in Example 3.

The release values of the cores and of the film-coated tablets in simulated gastric fluid are the same and are given in Table 1.

Example 7: Hard gelatin capsules containing 40 mg of nifedipine

Hard gelatin capsules are filled with the powder mixture according to Example 5 or the granules according to Example 6. The filling weight of the hard gelatin capsules is 150 mg. The capsules contain pigments, such as iron oxide/titanium oxide, to protect the nifedipine against the action of light.

The release values are given in Table 1.

Example 8: Film-coated tablets containing 40 mg of nifedipine

For the preparation of 900,000 tablets, 18 kg of HPMC 2208/4,000 cps (Methocel K4M or Metholose 90 SH 4,000), 36 kg of nifedipine having a specific surface area of 0.3–0.4 $m^2/g$ (BET), 36 kg of a commercially available unitary product consisting of 75% lactose and 25% powdered cellulose (Cellactose, Meggle) and 43.65 kg of microcrystalline cellulose are mixed together. For a ready-to-compress mixture, 1.35 kg of magnesium stearate and 0.675 kg of grinded colloidal silicon dioxide are separately added. The mixture is compressed to form tablets weighing 150.75 mg and having a diameter of 7.0 mm, a thickness of 4 mm and a hardness of about 70–80N.

The tablets are coated with 1.8 kg of HPMC 2910/15 cps, 1.8 kg of titanium dioxide, 0.81 kg of red ferric oxide, 0.99 kg of polyethylene glycol 400, and 0.9 kg of talc, and polished with 0.07 kg of polyethylene glycol 6000.

The release values of the cores and of the film-coated tablets in simulated intestinal fluid are the same and are given in Table 3 for 8 hours and Table 3a for 24 hours.

TABLE 3

Rates of release of nifedipine (mg/h and %) in simulated intestinal fluid during 8 h

| time h | mg/h | % |
|---|---|---|
| 0 | 0.0 | 0.0 |
| 1 | 1.24 | 3.1 |
| 2 | 1.32 | 6.4 |
| 3 | 1.36 | 9.8 |
| 4 | 1.44 | 13.4 |
| 5 | 1.36 | 16.8 |
| 6 | 1.48 | 20.5 |
| 7 | 1.44 | 24.1 |
| 8 | 1.36 | 27.5 |

Figure 1:
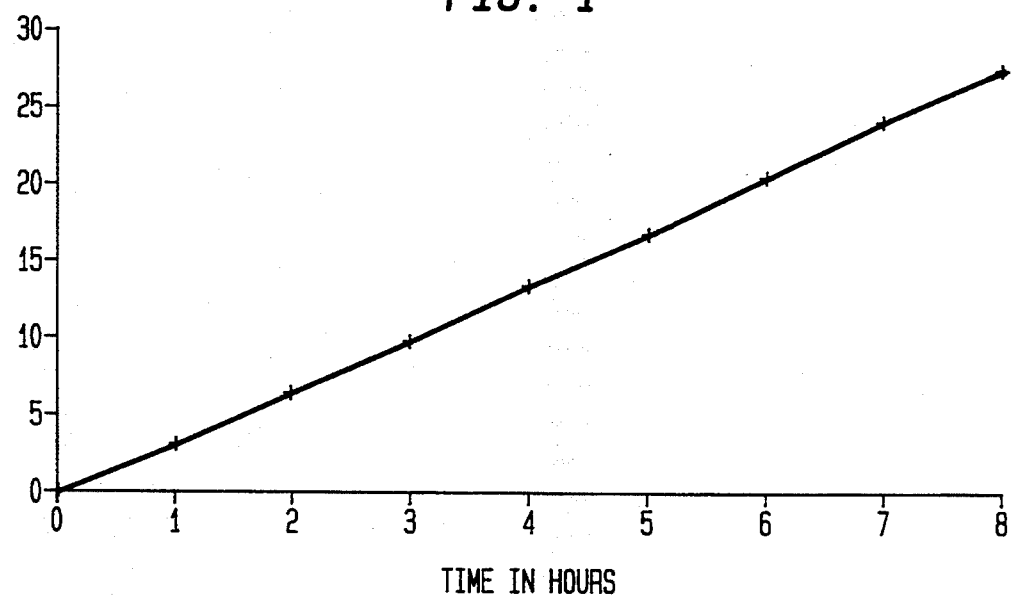
FIG. 1 shows the percentage of release of nifedipine up to 8 hours in vitro in simulated intestinal fluid (sif) from the tablet according to Example 8.

The percentages of release in simulated intestinal fluid of the Table 3 is represented by FIG. 1 and is in form of a linear curve of $0^{th}$ order.

TABLE 3a

Rates of release of nifedipine (mg/h and %) in simulated intestinal fluid during 24 h

| time h | mg/h | % |
|---|---|---|
| 0 | 0.0 | 0.0 |
| 2 | 1.00 | 5.0 |
| 4 | 1.05 | 10.3 |
| 6 | 1.10 | 15.7 |
| 8 | 1.05 | 21.0 |
| 10 | 1.10 | 26.3 |
| 12 | 1.25 | 32.5 |
| 14 | 1.70 | 41.0 |
| 16 | 1.55 | 47.3 |
| 18 | 1.95 | 57.1 |
| 20 | 1.75 | 65.9 |
| 22 | 1.50 | 73.2 |
| 24 | 1.50 | 80.5 |

Figure 2:
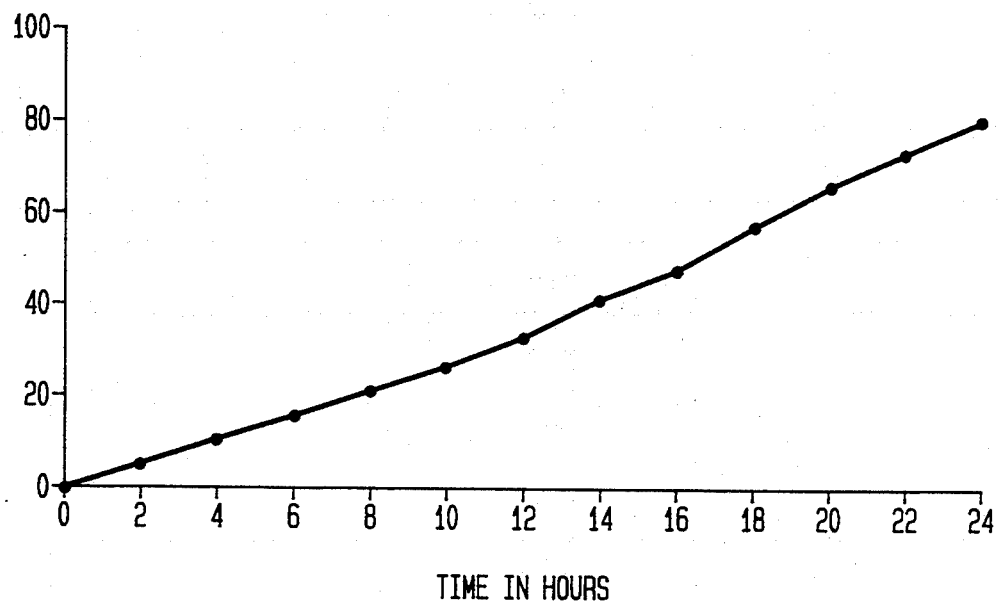
FIG. 2 shows the percentage of release of nifedipine up to 24 hours in vitro in simulated intestinal fluid (sif) from the tablet according to Example 8.

The percentages of release in simulated intestinal fluid of the Table 3a is represented by FIG. 2 and is in form of a linear curve of $0^{th}$ order.

The mean values for the plasma levels over a period of 48 hours in eighteen healthy human test subjects after p.o. administration of the 40 mg tablet are given in Table 4.

TABLE 4

Mean values (ng/ml) for plasma levels after a single administration of 40 mg nifedipine of Example 8

| time h | Example 8 40 mg |
|---|---|
| 0.0 | 0.00 |
| 0.5 | 1.20 |
| 1.0 | 4.60 |
| 2.0 | 9.50 |
| 2.5 | 11.20 |
| 3.0 | 12.00 |
| 4.0 | 13.60 |
| 6.0 | 15.70 |
| 8.0 | 14.00 |
| 10.0 | 13.90 |
| 12.0 | 15.00 |
| 24.0 | 13.30 |
| 26.0 | 10.10 |
| 28.0 | 8.40 |
| 34.0 | 3.70 |
| 36.0 | 2.70 |
| 48.0 | 1.10 |

The in vitro/in vivo correlation of released and absorbed (calculated according to Wagner-Nelson, J. pharm. Sci. 52, Vol. 6, 1963, page 610-611), nifedipine from the tablet of Example 8 is shown in FIG. 3.

Example 9: Tablets containing 40 mg of nitrendipine

For the preparation of 3,000 tablets, 30.0 g of HPMC 2208/100 cps (Methocel K100LV), 120 g of nitrendipine, 120 g of a commercially available unitary product consisting of 75% lactose and 25% powdered cellulose (Cellactose, Meggle) and 145.50 g of microcrystalline cellulose are mixed together.

For a ready-to-compress mixture, 4.5 g of magnesium stearate and 2.25 g of grinded colloidal silicon dioxide are separately added and the mixture is compressed to form tablets weighing 140.75 mg and having a diameter of 7.0 mm, a thickness of 4 mm and a hardness of 80N.

The tablets may be provided with the coating described in Example 3.

The release values of the cores and of the film-coated tablets in simulated gastric fluid are the same and are given in Table 5.

Example 10: Tablets containing 40 mg of nitrendipine

For the preparation of 3,000 tablets, 15.0 g of HPMC 2208/100 cps (Methocel K100LV), 120 g of nitrendipine, 135 g of a commercially available unitary product consisting of 75% lactose and 25% powdered cellulose (Cellactose, Meggle) and 145.50 g of microcrystalline cellulose are mixed together.

For a ready-to-compress mixture, 4.5 g of magnesium stearate and 2.25 g of grinded colloidal silicon dioxide are separately added and the mixture is compressed to form tablets weighing 140.75 mg and having a diameter of 7.0 mm, a thickness of 4 mm and a hardness of 80N.

The tablets may be provided with the coating described in Example 3.

The release values of the cores and of the film-coated tablets in simulated gastric fluid are the same and are given in Table 5.

TABLE 5

Rates of release (mg/h) of nitrendipine in simulated gastric fluid

| time h | Example 9 | | Example 10 | |
|---|---|---|---|---|
| | mg/h | % | mg/h | % |
| 0 | 0.00 | 0.0 | 0.00 | 0.0 |
| 2 | 0.37 | 3.7 | 0.40 | 4.0 |
| 4 | 0.37 | 7.5 | 0.49 | 8.9 |
| 6 | 0.36 | 11.1 | 0.50 | 14.0 |
| 8 | 0.38 | 15.0 | 0.48 | 18.8 |
| 10 | 0.35 | 18.5 | 0.44 | 23.2 |
| 12 | 0.32 | 21.7 | 0.40 | 27.6 |
| 13 | 0.29 | 24.6 | 0.35 | 30.6 |
| 16 | 0.26 | 27.2 | 0.32 | 33.8 |
| 18 | 0.23 | 29.5 | 0.31 | 36.9 |
| 20 | 0.20 | 31.4 | 0.30 | 39.8 |
| 22 | 0.20 | 33.4 | 0.26 | 42.5 |
| 24 | 0.19 | 35.3 | 0.28 | 45.3 |

I claim:

1. A pharmaceutical dosage form having prolonged release of zero order of an active ingredient upon once-daily oral administration, containing as active ingredient a therapeutically effective amount of a crystalline, dihydropyridine calcium antagonist having a solubility in water of from 0.0001 to 0.01%, a homogeneous matrix consisting of 5–60% by weight of the calcium antagonist, an hydroxypropylmethylcellulose of the 2208 USP XXII Class having a molecular weight in the range of about 20,000–250,000 in an amount sufficient to prolong the zero order release of the calcium antagonist and maintain a constant therapeutically effective plasma level over a period of 24 hours, said amount being from 2–50% by weight, and optionally 2–25% by weight of pharmaceutically acceptable excipients controlling release, said excipients being solid polyethylene glycols, polyvinylpyrrolidones, vinylpyrrolidone/vinylacetate cooolymers, pharmaceutically acceptable derivatives of vegetable fats in solid, tablet/table form having a melting point of above 60° C. or a combination thereof and optionally other pharmaceutically acceptable excipients making up the weight of the dosage form to 100%, said other pharmaceutically acceptable excipients being fillers, lubricants flow regulating agents or a combination thereof.

2. Pharmaceutical dosage form according to claim 1, wherein the calcium antagonist is nifedipine.

3. Pharmaceutical dosage form according to claim 1, wherein the calcium antagonist is nitrendipine.

4. Pharmaceutical dosage form according to claim 1, wherein the calcium antagonist is nimodipine, isradipine, nicardipine, niludipine, nigludipine, nisoldipine, felodipine, amlodipine or lacidipine.

5. Pharmaceutical dosage form according to claim 1, wherein the hydroxypropylmethylcellulose has a molecular weight of 20,000–120,000.

6. Pharmaceutical dosage form according to claim 1, wherein the dosage form contains 20, 30, 40, 50, 60, 70, 80, 90, 100 or 120 mg of active ingredient.

7. Pharmaceutical dosage form according to claim 1, wherein in vivo the active ingredient is released over a period of approximately 24 hours and the rate of release is constant over a period of up to 24 hours.

8. Pharmaceutical dosage form according to claim 1, wherein the release of the active ingredient has a delayed onset.

9. A pharmaceutical dosage form having prolonged release of zero order of an active ingredient upon once-daily oral administration, containing as active ingredient, crystalline nifedipine, wherein the dosage form comprises:
  (a) 40 mg of nifedipine;
  (b) 2–35 mg of hydroxypropylmethylcellulose of the 2208 USP XXII class having a molecular weight in the range of about 20,000–250,000 and having a viscosity of 100 or 4000 cps;
  (c) 20–50 mg of lactose and 35–60 mg of powdered or microcrystalline cellulose or both; or alternatively 40–80 mg of a mixture of 75% of lactose and 25% of powdered cellulose, with or without 48.5 mg of microcrystalline cellulose;
  (d) optionally 10 mg of hardened vegetable oil;
  (e) 1.5 mg of magnesium stearate; and
  (f) optionally 0.25–1 mg of highly dispersed silicon dioxide,
  such that said dosage forms prepared therefrom weigh 140–155 mg.

10. Pharmaceutical dosage form according to claim 9 wherein the dosage form is provided with a coating comprising:
  (a) 1.5–2.5 mg of titanium dioxide;
  (b) 0.5–1.5 mg of red iron oxide;
  (c) 1.0–3.0 mg of talc;
  (d) 2.0 mg of hydroxypropylmethylcellulose of the 2910 USP XXII class having a viscosity of 5 to 15 cps;
  (e) optionally 1–1.5 mg of polyethylene glycol 400;
  (f) optionally 0.005 mg of polysorbate 80;
  (g) optionally 0.5–0.75 mg of triethyl citrate; and
  (h) optionally 0.5–3.0 mg of methyl/ethyl acrylate.

11. A pharmaceutical dosage form having prolonged release of zero order of an active ingredient upon once-daily oral administration, containing as active ingredient, crystalline nitrendipine, wherein the dosage form comprises:
  (a) 40 mg of nitrendipine;
  (b) 2–35 mg of hydroxypropylmethylcellulose of the 2208 USP XXII class having a molecular weight in the range of about 20,000–250,000 and having a viscosity of 100 or 4000 cps;
  (c) 20–50 mg of lactose and 35–60 mg of powdered or microcrystalline cellulose or both; or alternatively 40–80 mg of a mixture of 75% of lactose and 25% of powdered cellulose, with or without 48.5 mg of microcrystalline cellulose;
  (d) optionally 10 mg of hardened vegetable oil;
  (e) 1.5 mg of magnesium stearate; and
  (f) optionally 0.25–1 mg of highly dispersed silicon dioxide,
  such that dosage forms prepared therefrom weigh 140–155 mg.

12. Pharmaceutical dosage form according to claim 11 wherein the dosage form is provided with a coating comprising:
  (a) 1.5–2.5 mg of titanium dioxide;
  (b) 0.5–1.5 mg of red iron oxide;
  (c) 1.0–3.0 mg of talc;
  (d) 2.0 mg of hydroxypropylmethylcellulose of the 2910 USP XXII class having a viscosity of 5 to 15 cps;
  (e) optionally 1–1.5 mg of polyethylene glycol 400;
  (f) optionally 0.005 mg of polysorbate 80;
  (g) optionally 0.5–0.75 mg of triethyl citrate; and
  (h) optionally 0.5–3.0 mg of methyl/ethyl acrylate.

13. A pharmaceutical dosage form having prolonged release of zero order of an active ingredient upon once-daily oral administration, containing as active ingredient, crystalline nifedipine, wherein the dosage form comprises:
  (a) a core containing
    (i) 40 mg of nifedipine;
    (ii) 20 mg of hydroxypropylmethylcellulose of the 2208 USP XXII class having a molecular weight in the range of about 20,000–250,000 and having a viscosity of 4000 cps;
    (iii) 40 mg of a mixture of 75% of lactose and 25% of powdered cellulose;
    (iv) 48.5 mg of microcrystalline cellulose;
    (v) 1.5 mg of magnesium stearate; and
  (b) a film coating for the core containing
    (i) 1 part by weight of hydroxypropylmethylcellulose of the 2910 USP XXII class having a viscosity of 5 mPas;
    (ii) 0.55 parts by weight of polyethylene glycol 400;
    (iii) 1 part by weight of titanium dioxide;
    (iv) 0.45 parts by weight of red iron oxide; and
    (v) 0.50 parts by weight of talc.

14. Pharmaceutical dosage form according to claim 13 wherein the nifedipine has a specific surface area of 0.2–0.5 m²/g.

15. A pharmaceutical dosage form having prolonged release of zero order of an active ingredient upon once-daily oral administration, containing as active ingredient, crystalline nifedipine, wherein the dosage form comprises:
  (a) a core containing
    (i) 40 mg of nifedipine;

(ii) 20 mg of hydroxypropylmethylcellulose of the 2208 USP XXII class having a molecular weight in the range of about 20,000–250,000 and having a viscosity of 4000 cps;
(iii) 40 mg of a mixture of 75% of lactose and 25% of powdered cellulose;
(iv) 48.5 mg of microcrystalline cellulose;
(v) 1.5 mg of magnesium stearate;
(vi) 0.75 mg of colloidal silicon dioxide; and
(b) a film coating for the core containing
(i) 1 part by weight of hydroxypropylmethylcellulose of the 2910 USP XXII class having a viscosity of 15 cps;
(ii) 0.55 parts by weight of polyethylene glycol 400;
(iii) 1 part by weight of titanium dioxide;
(iv) 0.45 parts by weight of red ferric oxide;
(v) 0.50 parts by weight of talc; and
(vi) 0.04 parts by weight of polyethylene glycol 6000.

16. Pharmaceutical dosage form according to claim 15 wherein the nifedipine has a specific surface area of 0.2–0.5 $m^2/g$.

17. A method for treating cardiovascular conditions which comprises orally administering a pharmaceutical dosage form according to claim 1 once daily to a patient.

18. Pharmaceutical dosage form according to claim 1 wherein the dosage form is provided with a coating having no retarding action, the coating comprising a polyeric film-former, a pigment, an anti-adhesive agent and a plasticizer.

19. Pharmaceutical dosage form according to claim 1, wherein the dosage form is provided with a coating producing a lag time, comprising a water-insoluble but water-permeable polymer.

* * * * *